United States Patent [19]

Ho

[11] Patent Number: 4,587,244
[45] Date of Patent: May 6, 1986

[54] AMIDINE BENZODIAZEPINES, METHODS FOR THEIR USE AND INTERMEDIATES

[75] Inventor: Chih Y. Ho, Lansdale, Pa.

[73] Assignee: McNeilab, Inc., Fort Washington, Pa.

[21] Appl. No.: 721,723

[22] Filed: Apr. 10, 1985

Related U.S. Application Data

[63] Continuation-in-part of Ser. No. 599,095, Apr. 11, 1984, Pat. No. 4,547,497.

[51] Int. Cl.⁴ .............................................. A61K 31/55
[52] U.S. Cl. ................................. 514/219; 260/243.3
[58] Field of Search ............ 260/239.38, 245.7, 243.3; 514/219

*Primary Examiner*—Glennon H. Hollrah
*Assistant Examiner*—D. L. Dinner
*Attorney, Agent, or Firm*—Benjamin F. Lambert

[57] ABSTRACT

Fused tetracyclic benzodiazepines of the formula (I):

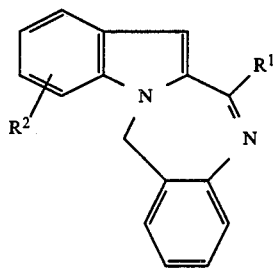

(I)

where $R^1$ is a cyclic amine such as 1-piperazine and $R^2$ is H or a substituent as defined herein are useful as antiovulatory and contragestational agents. Also, methods for their synthesis, intermediates used in such synthesis, methods for use as medicaments and pharmaceutical compositions are described.

2 Claims, No Drawings

AMIDINE BENZODIAZEPINES, METHODS FOR THEIR USE AND INTERMEDIATES

This is a continuation-in-part of application Ser. No. 599,095, filed Apr. 11, 1984 now U.S. Pat. No. 4,547,497.

Incidental to the study of acyl indoles, an indolo[2,1-c]-[1,4]benzodiazepine was prepared without mention of utility, see E. E. Garcia et al. in the Journal of Heterocyclic Chemistry, Volume 7, pages 1161–1163 (1970). Further, pyrrolo[2,1-c][1,4]benzodiazepines are described by W. B. Wright et al. in the Journal of Medicinal Chemistry, Vol. 23, No. 4, pages 462–465 (1980).

SUMMARY OF THE INVENTION

Indolo-benzodiazepines having an amidine function and defined by the following formula (I):

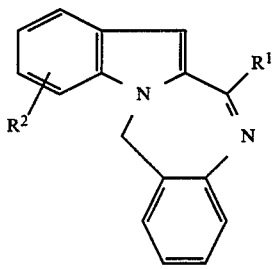

wherein $R^1$ is an amine function and $R^2$ is hydrogen or a moiety as herein defined. Also part of the invention are methods for the synthesis of formula (I) compounds, intermediates used in such syntheses, pharmaceutical compositions and methods for using such compositions, in particular methods for the treatment of allergic reactions.

DETAILED DESCRIPTION OF THE INVENTION

The compounds of the present invention are of the following formula (I):

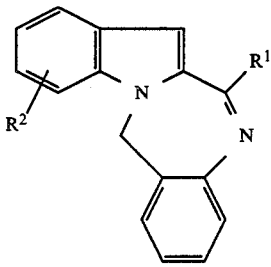

wherein $R^1$ is an amine function of the formula $-NR^3R^4$, 4-morpholino,

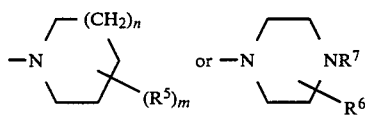

$R^2$ is hydrogen, alkoxy, alkyl, trifluoromethyl, halogen, nitro, hydroxy or dialkylamino;

$R^3$ and $R^4$ are independently hydrogen, alkyl or alkyl substituted by hydroxy, halogen or alkoxy;

m is 0 or 1;

n is 0, 1 or 2;

$R^5$ is hydroxy, alkyl, halogen, carboxy, alkoxycarbonyl or alkyl substituted by hydroxy, halogen, alkoxy or phenyl;

$R^6$ is hydrogen, alkyl, carboxy, alkoxycarbonyl or phenyl; and $R^7$ is hydrogen, alkyl, alkoxycarbonyl or alkyl substituted by hydroxy, halogen, alkoxy, phenoxy or alkoxycarbonyl, and the pharmaceutically acceptable salts thereof.

$R^2$, in particular, is hydrogen; alkoxy of about 1 to 6 carbons such as methoxy, ethoxy or isopropoxy; alkyl of about 1 to 6 carbons such as methyl, ethyl or tert-butyl; trifluoromethyl; halo such as fluoro, chloro, bromo or iodo; nitro; hydroxy; or dialkylamino of about 2 to 10 carbons such as dimethylamino and N-ethyl-N-methylamino.

$R^3$ and $R^4$ are, in particular, the same or different and are hydrogen; alkyl of about 1 to 6 carbons such as methyl, ethyl or n-propyl; or such an alkyl group substituted by a single substituent selected from the group consisting of hydroxy, fluoro, chloro, bromo, iodo or alkoxy of about 1 to 6 carbons, e.g., methoxy, ethoxy or iso-butoxy.

A particular value of n is 1.

$R^5$, in more detail, is hydroxy; alkyl of about 1 to 6 carbons such as methyl, ethyl or n-propyl; fluoro; chloro; bromo; iodo; carboxy; (alkoxy of about 1 to 6 carbons)carbonyl such as methoxycarbonyl; or alkyl of about 1 to 6 carbons substituted by a single substituent selected from the group of hydroxy, fluoro, chloro, bromo, iodo, alkoxy of about 1 to 6 carbons, such as methoxy or ethoxy, or phenyl. $R^5$ values are, when n is 1, in particular attached at the 4-position of the thus-defined piperidine ring with m as 1.

$R^6$, in more detail, is hydrogen; alkyl of about 1 to 6 carbons such as methyl, ethyl, n-propyl or n-butyl; carboxy; (alkoxy of about 1 to 6 carbons)carbonyl such as methoxycarbonyl or ethoxycarbonyl; or phenyl.

$R^7$, in particular, is hydrogen; alkyl of about 1 to 8 carbons such as methyl, ethyl, n-butyl or 3,4-dimethylpentyl; (alkoxy of about 1 to 6 carbons)carbonyl such as methoxycarbonyl or ethoxycarbonyl; or alkyl of about 1 to 8 carbons, such as methyl, ethyl, n-propyl or n-butyl, substituted by a single substituent selected from the group of hydroxy, fluoro, chloro, bromo, iodo, alkoxy of about 1 to 6 carbons, e.g., methoxy or ethoxy, phenoxy or (alkoxy of about 1 to 6 carbons)carbonyl, e.g., methoxycarbonyl or ethoxycarbonyl. A specific $R^7$ group is 3-hydroxypropyl.

Specific compounds of the present invention are the following:

12-(4-methyl-1-piperazinyl)-6H-indolo[2,1-c][1,4]-benzodiazepine;

12-(4-morpholinyl)-6H-indolo[2,1-c][1,4]benzodiazepine;

4-(6H-indolo[2,1-c][1,4]benzodiazepin-12-yl)piperazine-1-propanol;

12-(1-piperidinyl)-6H-indolo[2,1-c][1,4]-benzodiazepine;

12-(1-piperazinyl)-6H-indolo[2,1-c][1,4]-benzodiazepine;

12-(4-(ethoxycarbonyl)-1-piperazinyl)-6H-indolo[2,1-c][1,4]benzodiazepine;

12-(4-hydroxy-1-piperidinyl)-6H-indolo[2,1-c][1,4]benzodiazepine; and 12-(4-n-butyl-1-piperazinyl)-6H-indolo[2,1-c][1,4]benzodiazepine;

Salts may be formed by compounds of the invention with physiologicaly acceptable acids such as hydrochloric, hydrobromic, hydroiodic, perchloric, sulfuric, nitric, phosphoric, acetic, naphthalenesulfonic, propionic, glycolic, lactic, pyruvic, malonic, succinic, maleic, fumaric, malic, tartaric, citric, benzoic, cinnamic, madelic, methanesulfonic, ethanesulfonic, hydroxyethanesulfamic, benzenesulfonic, p-toluenesulfonic, cyclohexanesulfamic, salicylic, p-aminosalicylic, 2-phenoxybenzoic, 2-acetoxybenzoic or a salt made with saccharin. In addition, when a compound of formula (I) contains an $R^5$ or $R^6$ group which is a carboxy substituent a salt of the compound of formula (I) may be formed with a physiologically acceptable base such as sodium or potassium hydroxide or bicarbonate or an organic base such as tromethamine.

It is understood that compounds of formula (I) may exist in various isomeric forms, e.g., optical isomers formed in view of the different possible configurations of asymmetrical alkyl groups for $R^7$ such as 3-methyl-n-pentyl. The present invention includes all such individual isomers and racemates. In addition, compounds of formula (I) may exist in hydrated and solvated forms and the invention includes all such forms. As used in the present specification, "alkyl" and "alkoxy" moieties include straight and branched chain alkyl and alkoxy groups.

Compounds of the formula (I) as defined above may be prepared by reacting an intermediate of the formula (V)

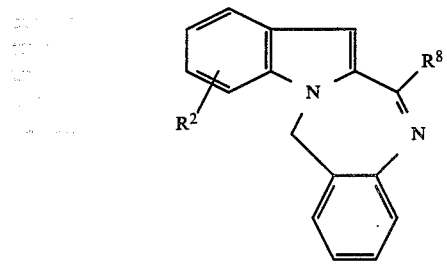

wherein $R^8$ is alkoxy or alkylthio of about 1 to 6 carbons or chloro and $R^2$ is as defined above, with an amine of the formula $HNR^3R^4$, morpholine,

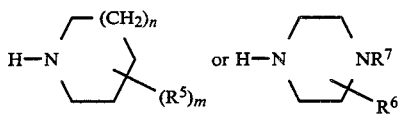

The reaction may take place at a temperature about 80° to 250° C., e.g. about 150° to 250° C. under superatmospheric pressure optionally in the presence of an acid catalyst such as acetic acid and/or a high boiling solvent such as xylene, particularly if the amine is not liquid at the reaction temperature. Preferably a large molar excess of the amine is used. For the synthesis of final products of the formula (I) wherein $R^7$ is other than hydrogen, the corresponding compound wherein $R^7$ is hydrogen may be reacted with a compound of the formula LG-$R^7$, where $R^7$ is as defined above but is other than hydrogen and LG is a leaving group such as chloro or bromo. The reaction with LG-$R^7$ may take place at about 0° to 120° C. in a solvent such as DMF.

Amine compounds of the formula $HNR^3R^4$,

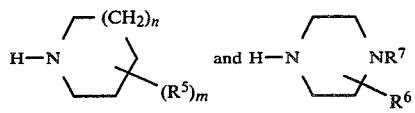

are known in the art or may be prepared from known compounds by simple reactions. For example, piperidines where n=1 may be prepared from the corresponding pyridines by hydrogenation with $H_2$ and a noble metal catalyst such as $PtO_2$, see Chapter 9 by H. S. Mosher in "Heterocyclic Compounds", Vol. 1, Ed. by R. C. Elderfield, John Wiley & Sons (1950).

The intermediate of formula (V) wherein $R^8$ is alkoxy or alkylthio may be prepared by first reacting an appropriately substituted alkyl 2-indolecarboxylate of the formula (II) with 2-nitrobenzyl chloride to yield the ester (III) wherein Y is $NO_2$ which is then reduced to the corresponding amine of formula (III) where Y is $NH_2$ and cyclized to the compound of formula (IV) wherein X is oxygen according to the following reaction scheme:

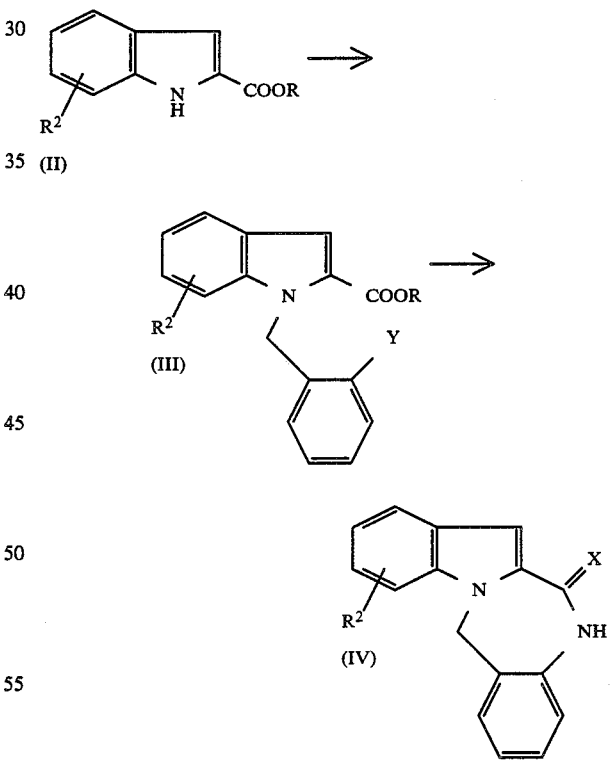

wherein R is alkyl of about 1 to 6 carbons, preferably about 1 to 3 carbons. Compounds of the formula (II) wherein $R^2$ is hydrogen, alkoxy, trifluoromethyl, halo, or dialkylamino may be prepared by the method of W. E. Noland in Organic Synthesis, Vol. 43, p. 40–45 (1963) using the appropriately substituted o-nitrotoluene as starting material. In addition, the Fisher indole synthesis may be used as described in "The Fisher Indole Synthesis" by Brian Robinson, John Wiley & Sons (1982). If $R^2$ is hydroxy, the methoxy indole may be prepared and deprotected with HBr or $BBr_3$ as known in the art. In addition, formula (II) compounds are known in the art and available commercially, see N. Bauman et al. in Biochemical Pharmacology, Vol. 18, pages 1241-1243 (1969) for $R^2$ as alkoxy, nitro, hydroxy, or halo; J. Bornstein et al. in the Journal of the American Chemical Society, Vol. 79, pages 1745-1748 (1957) for $R^2$ as trifluoromethyl; F. L. Allen et al. in Journal of the Chemical Society, pages 1283-1286 (1955) for $R^2$ as fluoro; U.S. Pat. Nos. 3,332,846, 4,053,624, 4,137,313, and 4,350,633; German OLS No. 1,948,507; and U.K. Patent Application No. 2,098,205 A published Nov. 17, 1982. Compounds of the formula (II) wherein R is alkyl may be prepared from the corresponding acids, i.e., R=H, by esterification with an alcohol and a catalytic amount of acid as known in the art. The $R^2$ substituent may be at the 4-, 5-, 6- or 7-position of the indole ring system.

In more detail, the reaction between the indole of formula (II) and 2-nitrobenzyl chloride may be conducted by first reacting the indole with a strong base such as sodium hydride at about $-78°$ to $60°$ C. in a dry solvent, e.g. DMF. The thus-produced anion of the indole is reacted with 2-nitrobenzyl chloride at an initial temperature of about $-78°$ to $25°$ C. and allowing the reaction to warm to room temperature. The ester (III) where Y is $NO_2$ is then converted to the amine of formula (III) where Y is $NH_2$ by reduction, e.g., by catalytic reduction with $H_2$ in a solvent such as methanol using a noble metal such as palladium or Raney nickel catalyst. The amino ester (III) where Y is $NH_2$ is then converted to the lactam of formula (IV) wherein X is oxygen by heating at about $100°$ to $200°$ C. with an amide-forming catalyst such as 2-hydroxypyridine.

The compound of formula (IV) where X is oxygen may be converted to an intermediate of formula (V) wherein $R^8$ is alkoxy by reaction with a Meerwein agent such as triethyloxonium fluoroborate in a solvent such as $CH_2Cl_2$ or diethylether at room temperature. Secondly, the compound of formula (IV) may be first converted to the corresponding thio compound, where X is a sulphur atom, by reaction with an agent such as phosphorus pentasulfide and a basic catalyst such as pyridine at a temperature of about $70°$ to $150°$ C. The compound of formula (IV) where X is sulphur may then be reacted with an alkylating agent such as methyl iodide or dimethyl sulfate in the presence of base catalysis, e.g., sodium hydroxide at a temperature of about $25°$ to $100°$ C. in a solvent such as methanol or dioxane to yield an intermediate of formula (V) where $R^8$ is alkylthio. Thirdly, a compound of formula (IV) wherein X is oxygen may be reacted with $PCl_5$ to yield the intermediate of formula (V) wherein $R^8$ is chloro which may then be reacted with the amine as described above. In a fourth embodiment of the synthesis of the final product (I), the intermediate of formula (IV) where X is oxygen is reacted with $TiCl_4$ and the amine to yield the final product directly by reaction at $0°$ to $150°$ C. in a solvent such as dioxane.

The synthesis of intermediates of the formula (IV) where X is oxygen is detailed in my copending application U.S. Ser. No. 540,262 filed Oct. 11, 1983, and now U.S. Pat. No. 4,529,724, which is hereby incorporated by reference.

It has been found that compounds of the invention show activity against allergic reactions in mammals according to the passive cutaneous anaphylaxis test described in "Handbook of Experimental Immunology", Ed. by D. M. Weir, Blackwell Scientific Publications, London, pages 21.1-21.6 (1978). In this test, passive cutaneous anaphylaxis (PCA) is induced in male Sprague-Dawley rats by an intradermal injection of 0.05 ml serum (rat antiovalbumen serum) obtained from rats previously sensitized with ovalbumen. Twenty-four hours post injection the rats are challenged intravenously with ovalbumen and Evans Blue dye in saline. Simultaneous intradermal injections of serotonin and histamine are made. Thirty minutes later the animals are sacrificed and the skin is reflected. Results are determined by measuring wheal sizes and scoring the color intensities relative to a standard color chart. The percent response is evaluated by taking (1-mean experimental value/mean control value)×100. Drugs were evaluated by intraperitoneal administration one hour pre-challenge. The response was evaluated 30 minutes after antigen administration.

In the PCA test, the compound produced in example 1d. was found to have an $ED_{50}$ of about 0.33 mg per kilogram of body weight p.o. and an i.p. $ED_{50}$ of about 0.17 mg per kilogram of body weight. In contrast, ketotifen was found to have an $ED_{50}$ value i.p. of 0.32 mg/kg of body weight and 2.4 mg/kg p.o. while oxatomide showed a p.o. $ED_{50}$ of 6.0 mg/kg and an i.p. $ED_{50}$ of 1.2 mg/kg.

A second test used for the invention compounds was the Active Lung Anaphylaxis Test conducted in a manner similar to tests described by D. M. Richie et al., in Agents and Actions, 11(4) pages 396-399 (1981); by R. Hicks et al, in the British J. of Pharmacology, 21, pages 441-449 (1963); and by H. O. J. Collier et al, in the British J. Pharm. Chemother., 30, pages 283-301 (1967). The basis of the test is the finding that extrinsic asthma is attributed to an antigen-induced, IgE-mediated mechanism. In this guinea pig lung anaphylaxis model a similar event is produced by an antigen-induced IgG-mediated mechanism. A specific antigen (chicken egg albumin) interacts with the IgG antibody which is fixed to a mast cell of the lung (basophils and other cell types may be also involved as well as mast cells) and results in the release of several chemical mediators. Bronchoconstriction is effected by this release. Histamine and leukotrienes (SRS-A) are thought to be the most potent bronchoconstrictors. However, eosinophil chemotactic factor of anaphylaxis, prostaglandins, bradykinin, serotonin, cholinergic agents and platelet activating factor may also mediate such a response.

In the Active Lung Anaphylaxis Test, guinea pigs are sensitized to egg albumin, 1 mg s.c., using Bordetella Pertussis vaccine (0.5 ml) as an adjuvant. Two weeks after sensitization, the animals are anesthetized with sodium pentobarbital, 65 mg/kg i.p. The trachea, jugular vein and carotid artery are cannulated for monitoring air way resistance, intravenous administration of test compounds and measuring mean arterial blood pressure, respectively. The animal is then challenged with egg albumin, 0,5 mg/kg i.v., producing an asthmatic reaction characterized by severe bronchoconstriction. The ability of compounds to inhibit this bronchoconstriction (measured as an increase in airway resistance) is evaluated by pretreatment with the compound prior to the egg albumin challenge. Compounds may also be evaluated using the oral route of administration.

In the Active Lung Anaphylaxis Test, the compound produced in Example 1d. was found to have an $ED_{50}$ of about 0.01 mg/kg of body weight i.v. while the compound produced in Example 3 was found to have an $ED_{50}$ of about 0.7 mg/kg i.v. In contrast, ketotifen had an $ED_{50}$ of 0.0002 mg/kg i.v. and oxatomide had a $ED_{50}$ of 1.25 mg/kg i.v.

In addition to their use as antiallergins, some of the compounds of this invention such as, for example 12-(4-methyl-1-piperazinyl)-6-H-indolo[2,1-C][1,4]benzodiazepine (McN 4923) and 4-(6H-indolo[2,1-C][1,4]benzodiazepin-12-yl)piperazine-1-propanol (McN 5019) for example inhibit ovulation and are useful as contragestational agents. The testing for the latter utilities was carried out as follows:

Adult cycling Sprague Dawley rats (200–250 g) obtained from Charles River Laboratories were treated orally on each of three days (metestrus, diestrus, proestrus) prior to expected ovulation with the test compound prepared in sesame oil. The vaginal cytology was examined daily and on the day of expected ovulation (estrus) the rats were sacrificed and the oviducts examined for the presence of ova.

In the contragestational test, adult female mice were cohabited with males and the following morning, those females in which a vaginal plug was found were designated day 1 of pregnancy. Each pregnant female received the test compound prepared in sesame oil orally each day for the first thirteen days of pregnancy. Approximately day 18–20 of pregnancy the females were sacrificed and examined for the presence and conditions of the implants.

RESULTS

In the antiovulatory screening test, McN 4923 prevented ovulation in three rats each when treated at 50, 25, 12.5, 5, 2.5 and 1 mg/kg administered orally on each of three days prior to expected ovulation. At 0.5 mg/kg, ovulation was inhibited in all ten rats similarly treated and at 0.1 mg/kg only 3 of 10 rats ovulated. This finding was confirmed when tested periodically over several months. Additional studies confirmed that McN 4923 was completely effective when a single dose of 0.5 mg/kg was given on the day of proestrus only.

In the mouse contragestational screening, 50 mg/kg of McN 4923 administered orally for the first thirteen days of pregnancy resulted in implants in 2 of 5 treated mice while 4 of 5 control vehicle treated mice had implants.

(McN 5019) was also found to inhibit ovulation in all five rats treated at 0.5 mg/kg in the initial screening protocol.

Also part of the present invention are pharmaceutical compositions and methods, e.g., for the treatment of allergic reactions or the inhibition of ovulation using such compositions. To prepare the pharmaceutical compositions of this invention, one or more compounds or salts thereof of the invention as the active ingredient, is intimately admixed with a pharmaceutical carrier according to conventional pharmaceutical compounding techniques, which carrier may take a wide variety of forms depending on the form of preparation desired for administration, e.g., oral, topical or parenteral. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient, and, preferably, from about 25 to about 100 mg.

For treatment of allergic reactions in an animal, compounds of the invention, may be administered orally or parentally in an amount of about 0.1 to 10 mg/kg of body weight per day, such be optionally divided into 2 equal doses in a day. For the inhibition of ovulation and interruption of pregnancy, the active compounds of this invention may be administered in an amount of about 0.1 to about 100 mg/kg of body weight.

Also, part of the present invention are the intermediates of the formula (IV) wherein X is a sulphur atom and formula (V) wherein $R^8$ is alkoxy or alkylthio.

In the following examples and throughout the specification, the following abbreviations may be used: mg (milligrams); g (grams); kg (kilograms); ml (milliliters); mmole (millimoles); $\mu M$ (micromolar); mM (millimolar); M (molar); N (normal); psi (pounds per square inch); mp (melting point); bp (boiling point); meq (milliequivalents); E (trans); Z (cis); $Et_2O$ (diethyl ether); EtOAc (ethyl acetate); MeOH (methanol); EtOH (ethanol); i-PrOH (isopropanol); LAH (lithium alminum hydride); THF (tetrahydrofuran); DMF (dimethylformide); p.o. (per os, orally); i.p. (intraperitoneal); s.c. (subcutaneous); i.v. (intravenous); and C,H,N,O, etc. (the chemical symbols for the elements). Unless otherwise indicated, all temperatures are reported in °C. (degrees centigrade).

EXAMPLE 1 a. 6H-Indolo[2,1-c][1,4]benzodiazepin-12(11H)-one

Formula (IV): X=O; $R^2$=H.

A mixture of 5.69g (0.237 mole) of sodium hydride and 200 ml of dry DMF was stirred under an atmosphere of $N_2$ and cooled with an ice-water bath. A solution of 42 g (0.226 mole) of ethyl 2-indolecarboxylate in 150 ml of dry DMF was added with stirring over a period of 1.5 hours and stirring was continued overnight at room temperature. The resulting solution was cooled to −65° C. with a dry-ice/acetone bath and a solution of 50 g (0.29 mole) of 2-nitrobenzyl chloride in 60ml of dry DMF was added. After addition, the reaction mixture was allowed to stir at room temperature overnight and then poured into a mixture of ice and water. A yellow solid was obtained by filtration and recrystallized from ethanol.

The above obtained yellow solid and 2 g of 10% Pd/C in 450 ml of MeOH was hydrogenated under 50 psi hydrogen pressure at room temperature until the uptake of hydrogen ceased. The catalyst was removed by filtration and the filtrate was evaporated in vacuo to yield a brown solid which was combined with 300 ml of xylene and 7 g of 2-hydroxypyridine and heated at reflux with a Dean Stark trap for 48 hours. The title compound was obtaied by filtration and recrystallized from i-PrOH/DMF to yield a white solid, mp 270°–272° C.

Elemental Analysis: Calculated for $C_{16}H_{12}N_2O$: C, 77.40; H, 4.87; N, 11.28. Found: C, 77.50; H, 5.04; N, 11.66.

b. 6H-Indolo[2,1-c][1,4]benzodiazepin-12(11H)-thione

Formula (IV): X=S; $R^2$=H.

A mixture of 15.84 g (0.064 mole) of 6H-indolo[2,1-c][1,4]benzodiazepine-12(11H)-one, the product of Example 1a., 7.68 g (0.032 mole) of phosphorous pentasulfide and 150 ml of pyridine was refluxed for 4 hours, cooled and then concentrated on a rotary evaporator to yield a gummy residue. The residue was treated with 1 M aqueous sodium carbonate to pH 7–7.2. The resulting yellow mixture was stirred for 24 hours at room temperature. The title compound, a yellow solid, mp 255°–260° C. (dec) was obtained by filtration in 65.7% yield.

c. 12-Methylthio-6H-indolo[2,1-c][1,4]benzodiazepine

Formula (V): $R^8$=SCH$_3$; $R^2$=H.

To a stirred solution of 1.53 g of 6H-indolo[2,1-c][1,4]-benzodiazepine-12(11H)-thione, the product of Example 1b., in 15 ml of dioxane was added simultaneously in four portions during the course of 1 hour, a solution of 1.93 g of potassium hydroxide in 10 ml of methanol and 2.21 g of dimethyl sulfate in 4 ml of methanol. The mixture was stirred overnight and then concentrated on a rotary evaporator to yield a residue. The residue was dissolved in methylene chloride and then washed with water and saturated sodium chloride solution. Removal of solvent in vacuo gave the title product, a yellow solid, mp 171°–173° C. The product was used without further purification.

Elemental Analysis: Calculated for $C_{17}H_{14}N_2S$: C, 73.35; H, 5.07; N, 10.06; S, 11.52. Found: C, 73.07; H, 5.28; N, 9.92; S, 11.40.

d. 12-(4-Methyl-1-piperazinyl)-6H-indolo[2,1-c][1,4]-benzodiazepine

Formula (I): $R^1$=—N(CH$_2$CH$_2$)$_2$NCH$_3$; $R^2$=H.

A mixture of 4.45 g of 12-methylthio 6H-indolo[2,1-c][1,4]benzodiazepine, the product of Example 1c and 18 ml of 4-methyl-1-piperazine was heated in a pressure bottle to 230° C. for 12 hours. Excess 4-methyl-1-piperazine was removed under reduced pressure. The residue was dissolved in methylene chloride and extracted with 5% hydrochloric acid solution. The extracted aqueous solution was neutralized with 1N sodium hydroxide solution and then extracted with methylene chloride. The organic solution was dried over sodium sulfate. Removal of solvent gave solid material which was recrystallized from methanol to give the title compound, an off-white solid, mp 179°–181° C.

Elemental Analysis: Calculated for $C_{21}H_{22}N_4$: C, 76.33; H, 6.71; N, 16.96. Found: C, 76.18; H, 6.69; N, 17.08.

EXAMPLE 2

12-(4-Morpholinyl)-6H-indolo[2,1-c][1,4]benzodiazepine monohydrochloride ethanolate Formula (I): $R^1$=—N(CH$_2$CH$_2$)$_2$O; $R^2$=H.

A mixture of 3.2 g of 12-methylthio 6H-indolo[2,1-c][1,4]benzodiazepine, the product of Example 1c., and 15 ml of morpholine in a pressurized bottle was heated to 215° C. for 12 hours. Excess morpholine was removed by evaporation in vacuo and the residue was recrystallized from EtOAc to yield 3.1 g of crude product. The crude product was dissolved in $Et_2O/CH_2Cl_2$ and treated with one equivalent of ethereal hydrogen chloride solution to give the hydrochloride salt. Recrystallization of the salt from EtOH gave the title compound as a colorless solid; mp 263°–265° C.

Elemental Analysis: Calculated for $C_{20}H_{19}N_3O.HCl.C_2H_5OH$: C, 66.07; H, 6.55; N, 10.51. Found: C, 66.11; H, 6.55; N, 10.50.

EXAMPLE 3

4-[6H-indolo[2,1-c][1,4]benzodiazepin-12-yl]piperazine-1-propanol

Formula (I): $R^1$=—N(CH$_2$CH$_2$)$_2$N(CH$_2$)$_3$OH; $R^2$=H.

A mixture of 5.39 g of 12-methylthio-6H-indolo[2,1-c][1,4]benzodiazepine, the product of Example 1c., and 17 g of 1-piperazinepropanol in a pressurized bottle was heated to 220° C. overnight. The reaction mixture was dissolved in CH$_2$Cl$_2$ and then was washed with water. Removal of solvent in vacuo followed by recrystallization from EtOH gave the title compound, a colorless solid, mp 174°–175° C.

Elemental Analysis: Calculated for $C_{23}H_{26}N_4O$: C, 73.77; H, 7.00; N, 14.96. Found: C, 73.68; H, 7.03; N, 14.92.

EXAMPLE 4

12-(1-Piperidinyl)-6H-indolo[2,1-c][1,4]benzodiazepine

Formula (I): $R^1$=—N(CH$_2$CH$_2$)$_2$CH$_2$; $R^2$=H.

A mixture of 3.0 g of 12-methylthio-6H-indolo[2,1-c][1,4]-benzodiazepine, the product of Example 1c., and 3.9 ml of piperidine in a pressurized bottle was heated to 230° C. for 20 hours. The reaction mixture was dissolved in EtOAc and washed with water. Removal of the solvent in vacuo and recrystallization of the residue from EtOH gave the title compound, a pale yellow solid, mp 178°–179° C.

Elemental Analysis: Calculated for $C_{21}H_{21}N_3$: C, 79.97; H, 6.71; N, 13.32. Found: C, 79.95; H, 6.72; N, 13.29.

Example 5

12-(1-Piperazinyl)-6H-indolo[2,1-c][1,4]-benzodiazepine (Z)-2-butenedioate (1:1)

Formula (I): $R^1$=—N(CH$_2$CH$_2$)$_2$NH; $R^2$=H.

A mixture of 5 g of 12-methylthio-6H-indolo[2,1-c][1,4]benzodiazepine, the product of Example 1c, and 7.78 g of piperazine in a pressurized bottle was heated to 230° C. for 10 hours. The reaction mixture was dissolved in CH$_2$Cl$_2$ and was extracted with 1M hydrochloric acid. The aqueous solution was neutralized with dilute ammonium hydroxide. The aqueous solution was extracted with CH$_2$Cl$_2$, the organic layer dried over anhydrous Na$_2$SO$_4$ and evaporated in vacuo to give the crude product. The crude product was treated with maleic acid to give the title compound salt which was recrystallized from t-BuOH to yield a beige solid, mp 205° C. (dec.)

EXAMPLE 6

12-[4-(Ethoxycarbonyl-1-piperazinyl)-6H-indolo[2,1-c][1,4]benzodiazepine 2-naphthalenesulfonate (1:1)

Formula (I): $R^1 = -N(CH_2CH_2)_2NCOOCH_2CH_3$; $R^2 = H$.

A mixture of 5.3 g of 12-methylthio-6H-indolo[2,1-c][1,4]-benzodiazepine, the product of Example 1c., 10.04 g of 4-(ethoxycarbonyl)-1-piperazine and 20 ml of xylene in a steel bomb vessel was heated to 230° C. for 16 hours. The reaction mixture was dissolved in $CH_2Cl_2$, washed with water, and dried over anhydrous $Na_2SO_4$. Solvent was evaporated in vacuo to yield a brown residue. Chromatographic purification through a silica gel column eluting with EtOAc/cyclohexane (1:2) followed by evaporation of the solvent in vacuo yielded a crude free base which was dissolved in $Et_2O$ and treated one equivalent of 2-naphthalenesulfonic acid to give the acid addition salt. Recrystallization from $Et_2O$/i-PrOH gave the title compound as a colorless solid, mp 226°–228° C.

Elemental Analysis: Calculated for $C_{23}H_{24}N_4O_2 \cdot C_{10}H_8O_3S$: C, 66.42; H, 5.41; N, 9.39. Found: C, 66.19; H, 5.46; N, 9.37.

EXAMPLE 7

12-(4-Hydroxyl-1-piperidinyl)-6H-indolo[2,1-c][1,4]benzodiazepine

Formula (I): $R^1 = -N(CH_2CH_2)_2CHOH$; $R^2 = H$.

A mixture of 18.8 g of 12-methylthio-6H-indolo[2,1-c][1,4]benzodiazepine, the product of Example 1c., 17 g of 4-hydroxy-1-piperidine and 50 ml of xylene in a steel bomb vessel was heated to 235° C. for 4 hours. The resulting solution was dissolved in EtOAc, washed with water and dried over anhydrous $Na_2SO_4$. The crude reaction product was purified through a silica gel column eluting with EtOAc. The crude product was recrystallized from MeOH/iPrOH to yield the title compound, a white solid, mp 197°–200° C.

Elemental Analysis: Calculated for $C_{21}H_{21}N_3O$: C, 76.11; H, 6.39; N, 12.68. Found: C, 76.11; H, 6.43; N, 12.67.

EXAMPLE 8

12-(4-n-Butyl-1-piperazinyl)-6H-indolo[2,1-c][1,4]benzodiazepine (E)-2-butenedioate (2:1)

Formula (I): $R^1 = -N(CH_2CH_2)_2N(CH_2)_3CH_3$; $R^2 = H$.

A mixture of 7.1 g of 12-methylthio-6H-indolo[2,1-c][1,4]benzodiazepine, the product of Example 1c, 6.64 g of 4-n-butyl-1-piperazine and 20 ml of xylene in a pressure bottle was heated to 240° C. for 3 hours. The reaction mixture was dissolved in EtOAc, washed with water, and dried anhydrous over $Na_2SO_4$. The crude product (after removal of solvent) was dissolved in MeOH and treated with one equivalent of fumaric acid to give a solid. Recrystallization of the fumarate salt from DMF yielded the title compound, a colorless solid, mp 197° C. (dec).

Elemental Analysis: Calculated for $C_{24}H_{28}N_4 \cdot 1/2C_4H_4O_4$: C, 72.53; H, 7.02; N, 13.01. Found: C, 72.50; H, 7.06; N, 13.02.

EXAMPLE 9

The unsubstituted piperazine product of Example 5 may be converted to other compounds of formula (I) by reaction with 3-chloro-n-propanol, ethyl chloroformate or ethylene oxide to at about 0° to 120° C. in a solvent such as DMF to yield, a compound of formula (I) wherein $R^1$ is a piperazine moiety, $R^6 = H$ and $R^7$ is $-(CH_2)_3OH$, $-COOCH_2CH_3$ or $(CH_2)_2OH$ respectively.

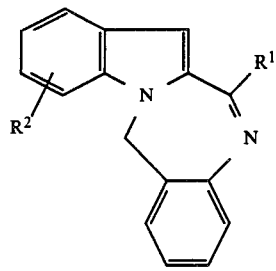

What is claimed is:

1. A method for inhibiting ovulation which comprises administering to a mammal an effective amount of a benzodiazepine of the formula:

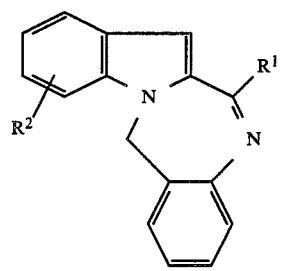

wherein $R^1$ is an amine function of the formula;

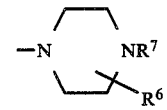

$R^2$ is hydrogen, alkoxy of about 1 to 6 carbons, alkyl of about 1 to 6 carbons, trifluoromethyl, halogen, nitro, hydroxy or dialkylamino of about 2 to 10 carbons;

$R^6$ is hydrogen, alkyl of about 1–6 carbons, carboxy, alkoxycarbonyl wherein the alkoxy group contains 1–6 carbons or phenyl; and $R^7$ is hydrogen, alkyl of about 1 to 8 carbons, alkoxycarbonyl wherein the alkoxy group contains 1 to 6 carbons or alkyl of about 1 to 8 carbons substituted by a single substituent selected from the group consisting of hydroxy, fluoro, chloro, bromo, iodo, alkoxy of about 1 to 6 carbons, phenoxy or alkoxycarbonyl wherein the alkoxy group contains 1 to 6 carbons, and the pharmaceutically acceptable salts thereof, in association with a pharmaceutically acceptable diluent or carrier.

2. A method of preventing implantation which comprises administering to a mammal an effective amount of a benzodiazepine of the formula:

wherein

R[1] is an amine function of the formula:

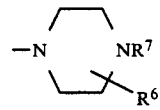

R[2] is hydrogen, alkoxy of about 1 to 6 carbons, alkyl of about 1 to 6 carbons, trifluoromethyl, halogen, nitro, hydroxy or dialkylamino of about 2 to 10 carbons;

R[6] is hydrogen, alkyl of about 1-6 carbons, carboxy, alkoxycarbonyl wherein the alkoxy ground contains 1-6 carbons or phenyl; and R[7] is hydrogen, alkyl of about 1 to 8 carbons, alkoxycarbonyl wherein the alkoxy group contains 1 to 6 carbons or alkyl of about 1 to 8 carbons substituted by a single substituent selected from the group consisting of hydroxy, fluoro, chloro, bromo, iodo, alkoxy of about 1 to 6 carbons, phenoxy or alkoxycarbonyl wherein the alkoxy group contains 1 to 6 carbons, and the pharmaceutically acceptable salts thereof, in association with a pharmaceutically acceptable diluent or carrier.

* * * * *